United States Patent [19]

Kopolow et al.

[11] Patent Number: 5,223,247
[45] Date of Patent: Jun. 29, 1993

[54] HAIR SPRAY COMPOSITION CONTAINING WATER SOLUBLE ALKYLATED PVP COPOLYMERS AS HAIR FIXATIVE THEREIN

[75] Inventors: Stephen L. Kopolow, Plainsboro; Edward W. Walls, Jr., Cranford; Robert B. Login, Oakland, all of N.J.; Mohammed Tazi, Marietta, Ga.

[73] Assignee: ISP Investments Inc., Wilmington, Del.

[21] Appl. No.: 820,819

[22] Filed: Jan. 15, 1992

[51] Int. Cl.$^5$ ............................................... A61K 7/11
[52] U.S. Cl. ..................................... 424/47; 132/202; 132/203; 424/70; 424/71; 424/78.02; 424/78.24; 424/DIG. 1; 424/DIG. 2; 514/772.5
[58] Field of Search ................... 424/47, 70, 71, 78.02, 424/78.24, DIG. 1, DIG. 2; 514/772.5; 132/202, 203

[56] References Cited

U.S. PATENT DOCUMENTS 4,640,709 2/1987 Beestman ........................... 71/100
5,002,075 3/1991 Kellett et al. ..................... 132/108

Primary Examiner—Thurman K. Page
Assistant Examiner—Robert H. Harrison
Attorney, Agent, or Firm—Walter Katz; Marilyn J. Maue; Joshua J. Ward

[57] ABSTRACT

A hair spray composition is provided herein which is capable of delivering a fine finishing mist at a high resin solids level. The composition is substantially moisture resistant, provides a stiff resin film having excellent hair holding power, and has a relatively low concentration of volatile organic compounds therein. The composition of the invention attains its unique attributes by including therein a water soluble or dispersible alkylated polyvinylpyrrolidone (PVP) copolymer powders having a predetermined blend of two monomer components, one being PVP having a defined molecular weight (K-value 15-120, preferably 30-90) and concentration (80-99%, preferably 90-95%) and the other being an alkylene having a selected number of carbon atoms ($C_4$-$C_{10}$, preferably ($C_6$-$C_8$), linear or branched, in a defined concentration (1-20%, preferably 5-10%).

4 Claims, No Drawings

HAIR SPRAY COMPOSITION CONTAINING WATER SOLUBLE ALKYLATED PVP COPOLYMERS AS HAIR FIXATIVE THEREIN

BACKGROUND OF THE INVENTION

1. Field of the Invention

This invention relates to hair spray compositions, and more particularly, to compositions which contain a water soluble or dispersible alkylated PVP copolymer as hair fixative therein.

2. Description of the Prior Art

Present hair spray compositions, both pump spray and aerosol spray formulations, are described in detail in U.S. Pat. Nos. 3,145,147; 4,223,009; and 4,521,402. These compositions generally perform effectively in providing most of the properties considered desirable for hair preparation, including fine spray patterns, prolonged curl retention under humid conditions, good holding power, ease of removability, and resistance to build-up. However, these and other pump formulations available in the art contain a considerable amount of alcohol which is a volatile organic compound (VOC). Aerosol hair spray formulations also require hydrocarbons or other propellants which add to the VOC content of the composition. Recent state legislation, moreover, has required that hair spray compositions have a lower VOC level than is presently found in commercial hairspray compositions. More particularly, it is now necessary that such compositions contain VOC materials at a weight level of no more than 80% of the composition.

Accordingly, it is an object of the present invention to provide new hair spray compositions which meet VOC standards while retaining the effective properties of presently available compositions for hair preparation and treatment.

Another object of the invention is to provide hair spray resin compositions capable of providing a fine finishing mist at a high resin solids level and which is substantially moisture resistant, also forms a stiff resin film on the hair of the user, and provides a good hold and curl retention, and which composition has a substantially reduced VOC level, particularly a lower alcohol concentration in pump formulations, and, a low level of alcohol and propellant components in aerosol-based formulations.

A particular object of the invention is to provide a hair spray composition containing water soluble alkylated PVP copolymers as hair fixative therein, which can be formulated to meet VOC standards.

These and other objects and features of the invention will be made apparent from the following more particular description thereof.

SUMMARY OF THE INVENTION

A hair spray composition is provided herein which is capable of delivering a fine finishing mist at a high resin solids level. The composition is substantially moisture resistant, provides a stiff resin film having excellent hair holding power, and has a relatively low concentration of volatile organic compounds therein. The composition of the invention attains its unique attributes by including therein a water soluble or dispersible alkylated polyvinylpyrrolidone (PVP) copolymer powders having a predetermined blend of two monomer components, one being PVP having a defined molecular weight (K-value 15-120, preferably 30-90) and concentration (80-99%, preferably 90-95%) and the other being an alkylene having a selected number of carbon atoms ($C_4$-$C_{10}$, preferably $C_6$-$C_8$), linear or branched, in a defined concentration (1-20%, preferably 5-10%).

The pump hair spray resin composition of the invention consists essentially of:

(a) said water soluble or dispersible alkylated PVP copolymer powder, in an amount of about 0.5-10% by weight;

(b) water in an amount of about 10-99% by weight; and (c) alcohol in an amount of about 0-60% by weight of the composition.

In the form of an aerosol, the hair spray resin composition of the invention consists essentially of about 50-80% by weight of the concentrate as defined above and about 20-50% by weight of a suitable propellant.

In the preferred form of the invention, (a) is a copolymer derived from the copolymerization of vinylpyrrolidone monomer (K 30-90, 90-95%) and an alkylene monomer ($C_6$-$C_8$, 5-10%) in the amount of about 3-8%; (b) is present in an amount of about 50-95%; and (c) is ethanol in the amount of about 5-50%, by weight of the composition.

DETAILED DESCRIPTION OF THE INVENTION

The pump hair spray composition of the present invention comprises:

|     | Component | Suitable | Preferred |
| --- | --- | --- | --- |
| (a) | Water soluble alkylated PVP copolymer | | |
|     | (1) PVP | K = 15-120<br>80-99% | K = 30-90<br>90-95% |
|     | (2) Alkylene | $C_4$-$C_{10}$<br>1-20% | $C_6$-$C_8$<br>5-10% |
|     | Concentration (% by weight) | 0.5-10 | 3-8 |
| (b) | Water (% by weight) | 10-99 | 50-95 |
| (c) | Alcohol (% by weight) | 0-60 | 5-50 |
|     | The aerosol hair spray composition comprises: | | |
| (1) | Hair spray concentrate | 50-80% 60-70% | 65% |
| (2) | Propellant | 20-50% 30-40% | 35% |

Suitable aerosol propellants include aliphatic hydrocarbons, e.g. butane, propane; $CO_2$, nitrous oxide, dimethylether and difluoroethane, and mixtures thereof.

A preferred copolymer resin for use in the hair spray composition of the invention is:

Ganex ® 904 (International Specialty Products, Wayne, N.J.) which is a water soluble copolymer powder derived from the copolymerization of 90% vinylpyrrolidone (K-30) and 10% butylene in t-butylperoxide.

EXAMPLE 1

The following composition of the invention was prepared and tested for effectiveness as a pump hair spray product.

| | EXAMPLE NO. | | | | | |
| --- | --- | --- | --- | --- | --- | --- |
| | 1 | 2 | 3 | 4 | 5 | 6 |
| Component | | | Wt. % | | | |
| Ganex ® 904<br>(PVP K-30, 90%, and | 5.0 | 8.0 | 3 | 3 | 5 | 5 |

-continued

| Component | EXAMPLE NO. | | | | | |
|---|---|---|---|---|---|---|
| | 1 | 2 | 3 | 4 | 5 | 6 |
| | Wt. % | | | | | |
| Butylene 10%) | | | | | | |
| Ethanol | — | — | 8 | 19 | 19 | 47.5 |
| Water | 95 | 92 | 89 | 78 | 76 | 47.5 |
| | 100.0 | 100.0 | 100.0 | 100.0 | 100.0 | 100.0 |

The above formulations were one-phase systems. Upon testing as a pump hair spray, they were observed to develop spray patterns which were fine, broad and dry. The curl retention properties at 90% RH and 80° F. were excellent even after 90 minutes.

EXAMPLE 2

PVP (K-15), PVP (K-60), PVP (K-90) and PVP (K-120) were substituted for PVP (K-30) in the compositions of Example 1. The hair spray formulations thus produced exhibited water solubility, good viscosity and gave excellent spray patterns.

PROCEDURE FOR PREPARING COMPOSITIONS OF INVENTION

A. Pump Spray

The pump hair spray compositions of the invention were prepared by first providing an ethanol solution including the neutralizing agent and dissolving the resin therein. Then the requisite amount of water was added. The composition then was packaged into a plastic bottle fitted with a suitable pump actuator, such as the commercial Calmar Mark II pump actuator.

B. Aerosol Compositions

The aerosol hair spray resin compositions of the invention were prepared from 65% by weight of the concentrate of the pump spray formulation of Example 1 and a 35% by weight of dimethylether propellant.

In summary, the structure of the alkylene used herein, linear or branched, can play an important role in the stiffness of the resin film. Use of a branched alkylene herein promotes a stiffer resin film in the presence of water, whereas a linear alkylene provides a softer film.

While the invention has been described with particular reference to certain embodiments thereof, it will be understood that changes and modifications may be made which are within the skill of the art. Accordingly, it is intended to be bound only by the following claims, in which:

What is claimed is:

1. A moisture resistant hair spray composition consisting essentially of
    (a) about 3-8% of a water soluble or dispersible alkylated polyvinylpyrrolidone copolymer powder comprising:
        (10 about 90-95% polyvinylpyrrolidone having a K-value of 30-90, and
        (2) 5-10% of an alkylene having 4 carbon atoms,
    (b) about 50-95% water; and
    (c) about 0-60% alcohol.
2. A hair spray composition according to claim 1, in which:
    (a) (1) is 90% , and
    (a) (2) is 10%.
3. A hair spray composition according to claim 2, in which:
    (a) (1) has a K-value of 30.
4. A hair spray composition according to claim 1 wherein (c) is present in the amount of about 5-50% by wieght of the composition.

* * * * *